(12) United States Patent
Jacobs et al.

(10) Patent No.: US 7,256,045 B2
(45) Date of Patent: Aug. 14, 2007

(54) ANALYZER WITH SAMPLE QUALITY MEASUREMENT, AND METHOD

(75) Inventors: Merrit N. Jacobs, Fairport, NY (US); James D. Shaw, Hilton, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 10/940,915

(22) Filed: Sep. 14, 2004

(65) Prior Publication Data
US 2005/0054112 A1   Mar. 10, 2005

Related U.S. Application Data

(62) Division of application No. 09/658,356, filed on Sep. 11, 2000, now Pat. No. 6,797,518.

(51) Int. Cl.
*G01N 35/00* (2006.01)

(52) U.S. Cl. .................... 436/43; 436/180; 422/99; 422/100; 422/101; 422/102; 422/64

(58) Field of Classification Search ............ 422/63–64, 422/67, 68.1, 81, 82.05, 82.09, 99–102, 104; 436/54, 46, 164, 165, 180, 171, 49, 43; 356/244, 356/315
See application file for complete search history.

(56) References Cited

U.S. PATENT DOCUMENTS 3,992,158 A * 11/1976 Przybylowicz et al. ....... 422/57

(Continued)

FOREIGN PATENT DOCUMENTS

| EP | 0 864 867 B1 | 3/1998 |
| WO | 92/20778 A1 | 11/1992 |
| WO | 99/47261 A1 | 11/1999 |

OTHER PUBLICATIONS

U.S. Appl. No. 09/910,399, filed Jul. 20, 2001, LaCourt.

(Continued)

*Primary Examiner*—Jill Warden
*Assistant Examiner*—Jyoti Nagpaul

(57) ABSTRACT

A system for detecting and analyzing patient sample quality and/or analytes, while the sample is in the metering tip used to aspirate the sample liquid from an original patient sample container, and also to dispense the liquid onto a slide test element. Spectrophotometric analysis may be done on the sample liquid while it is still in the tip which has been converted into a cuvette. One technique for such analysis is by scanning the cuvette for transmittance in a light-tight enclosure. Near-infrared and adjacent visible radiation may be used, and the absorption spectra of the liquid detected and analyzed. A possible aspect of the present invention relates to enhancing throughput of an analyzer by conducting a sample quality measurement in a process that is parallel to the main analyzer timing cycle. Another possible aspect of the present invention relates to improving performance of the analyzer by sealing the end of the metering tip to spontaneously form a cuvette for holding the sample during the sample quality measurement. Some advantages of the present system and method include improved throughput, the capability to use smaller sample liquid volumes, eliminating any need for a separate supply of cuvettes independent of the metering tips, and providing for detection through a cone of the metering tip rather than through any label, compared to doing the scanning of the sample liquid in a primary patient collection container.

1 Claim, 7 Drawing Sheets

U.S. PATENT DOCUMENTS

| | | | |
|---|---|---|---|
| 4,340,390 A | * | 7/1982 | Collins et al. ................ 436/54 |
| 4,420,254 A | * | 12/1983 | Smeaton ..................... 356/246 |
| 5,441,895 A | * | 8/1995 | Jakubowicz et al. ........ 436/518 |
| 5,734,468 A | * | 3/1998 | McNeal ...................... 356/319 |
| 5,846,492 A | * | 12/1998 | Jacobs et al. ................. 422/67 |
| 6,013,528 A | * | 1/2000 | Jacobs et al. ................. 436/54 |
| 6,797,518 B1 | | 9/2004 | Jacobs et al. |
| 2002/0110487 A1 | * | 8/2002 | Samsoondar ................ 422/63 |

OTHER PUBLICATIONS

U.S. Appl. No. 10/185,613, filed Jun. 28, 2002, Jakubowicz.

Translation for "Injection Nozzle Also Used As A Photometric Cell For An Automatic Analyzer" Japan Patent Agency, Gazette for Unexamined Patents; Kokai 61-164143 (1986).

* cited by examiner

ANALYZER WITH SAMPLE QUALITY MEASUREMENT, AND METHOD

CROSS RELATED TO RELATED APPLICATIONS

This application is a divisional application of U.S. Ser. No. 09/658,356, filed Sep. 11, 2000 now U.S. Pat. No. 6,797,518.

BACKGROUND AND SUMMARY OF THE INVENTION

1. Technical Background

The present invention relates generally to systems and methods for analyzing patient samples.

2. Discussion

Spectrophotometric analysis is often applied to liquid samples to determine their contents. In general, the term "spectrophotometric" refers to capturing spectral response over a range of wavelengths and correlating a response for each of the wavelengths. A device that performs this analysis is referred to as a "spectrophotorheter." Such spectrophotometric analysis has been performed with near-infrared and adjacent visible radiation, which is capable of ascertaining hemoglobin, glucose, albumin, lipoproteins, and many other sera components.

One challenge in performing spectrophotometric analysis has been that the samples are initially obtained in a variety of primary patient collection containers. These containers are usually tubes of varying diameters and lengths. In the case of a patient blood sample, the liquid is often centrifuged to separate the liquid serum or plasma from the cellular phases. Such tubes may have a patient identification label, varying and unpredictable amounts of the sera to be analyzed in the total sample, and contain a relatively large amount of sample liquid.

Prior spectrophotometric analysis systems are adequate to meet their design criteria, and they generally aliquot a portion of the sample into a secondary container or tube of a consistent size. This technique may add complexity and increase the time required for processing in a single sample. This measure may introduce additional equipment expenses and processing delays, and may involve spectrophotometric scanning through the patient label.

Examples of successful analyzers having a spectrophotometric measurement through the metering tip are shown in (i) U.S. Pat. No. 5,846,492, entitled "Sample Quality Measurement And/Or Analyte Measurement In Dispensing Tip Of An Analyzer," issued to Jacobs et al. on Dec. 8, 1998; and also (ii) U.S. Pat. No. 6,013,528, entitled "Analyzer Throughput Featuring Through-The-Tip Analysis," issued to Jacobs et al. on Jan. 11, 2000, which are both incorporated by reference.

Many clinical analyzers provide a generally serial or linear path of dependent events for processing each sample. This serial procedure is generally required to be performed in a specific order, and each step must be finished before the next can begin. For example, an analyzer process might include the steps of sample handling, aspirating a portion of the sample into a metering tip, dispensing a portion of the sample onto a test element or slide, and then disposing of the tip. The time required to completely process a single sample may be referred to as the processing time, and each step of the total time can be referred to as a timing cycle or the "heartbeat."

Such an analyzer might include various components, including a sample handling bin or repository for holding primary collection containers, a metering probe or proboscis which can move around the stations of the analyzer, one or more preferably disposable tips attached to the proboscis, and a metering pump connected to the proboscis for creating partial vacuum or partial pressure to selectively suck up into the tip or dispense a specific amount of sample liquid. In addition, analyzers often include the components required for a thin film or wet chemistry system, such as a test element supply, an incubator, reagent and assay supply, etc.

It is desirable in general to minimize the amount of the sample required for use in an analyzer, because any portion of the sample that is used for a particular operation cannot be later used for another process or operation. When the analyzer is in use, the component that actually touches the liquid of the sample is the tip.

Many of the metering tips used in analyzers are disposable, though the tip may also be permanent. Disposable tips generally have a relatively narrow cylindrical end, connected to a small cone, which is in turn connected to a larger generally cylindrical body. For optimum accuracy of the reading, and to minimize the amount of sample necessary, it is desirable to do the spectrophotometric measurement through the intermediate cone of the metering tip.

As an example, the present invention will be described in relation to clinical analyzers and sample quality measurement. However, it should be understood that the present invention relates to any apparatus or method having the features of the present invention, and is not limited to a particular type of design.

One method of incorporating a sample quality capability into an analyzer might be to insert a sample quality measurement step in between the step of aspirating the sample into the tip, and the step of dispensing the sample onto the test element. However, the sample quality measurement might take as long as the amount of time to meter the sample onto the test element. This particular method would therefore undesirably increase the length of the timing cycle of the analyzer. In addition, this particular method would undesirably require initially aspirating a larger portion of the sample, to raise the liquid level into the intermediate cone of the metering tip. Moreover, this technique may require substantial enabling software to move the metering tip to a new location for the sample integrity reading.

Accordingly, the present invention preferably provides systems and methods for analyzing and/or detecting the sample and/or analytes, while the sample is in the metering tip used to aspirate the sample liquid and also dispense it onto a slide test element. In other words, the spectrophotometric analysis may be done on the sample liquid while it is still in the tip which may be converted into cuvette, without requiring an additional container or cuvette, and may include a measurement of sample quality.

A possible aspect of the present invention relates to enhancing throughput of an analyzer by conducting a sample quality measurement in a process that is parallel to the main analyzer timing cycle. The sample quality measurement may thus be arranged after a portion of the sample has already been dispensed onto the test element, and after the metering tip has been removed from a proboscis. This novel method would eliminate a need for the analyzer to extend or skip a timing cycle, and may also eliminate a need for additional sample volume.

One possible way to conduct the spectrophotometric measurement after the metering tip is removed from the proboscis is to first seal or crimp the end of the metering tip, spontaneously forming a cuvette for holding the remaining portion of the sample during the measurement.

An improved analyzer process according to the principles of the present invention may include the steps of sample handling, aspirating a portion of the sample into a metering tip, and dispensing a portion of the sample onto a test element or slide. Next, a proboscis holding the metering tip may move to a tip ejection position. Then, a position sensor may be used to detect that the proboscis and metering tip have moved to the tip ejection position, and the sensor may trigger a clamp to hold the tip in position while the proboscis lifts away. Preferably after a short delay to let the sample fluid settle, a spectrophotometer reading is taken through the cone of the tip. The clamp may then be released, allowing the tip to fall into a disposal container.

In optional steps, a metering pump may pull sample fluid a short distance up into the tip to form a small bubble of air at the tip's end, and the end of the metering tip may be sealed to form a virtual cuvette.

Another optional step of the present invention may involve aspirating a selected auxiliary volume of sample liquid from the tip or cuvette after the sample quality measurement, and passing this auxiliary sample to a wet chemistry analyzer system. Or, rather than a wet chemistry system, the auxiliary sample may be passed to a diluter system, where it is diluted and passed on to the sample processing apparatus for repeating at least one clinical chemistry test and analysis on the diluted liquid.

Accordingly, some advantages of the present system and method include improved throughput, the capability to use much smaller sample liquid volumes, eliminating any need for a separate supply of cuvettes in addition to the metering tips. An additional advantage lies in providing for detection through a cone of the metering tip, rather than through any label that may be on a primary patient collection container.

Additional advantages of the present invention include conducting spectrophotometric analysis in a simpler and less expensive manner. Another advantage lies in obtaining results of spectrophotometric analysis in less time, without extending or omitting a timing cycle.

These and various other objects, advantages and features of the invention will become apparent from the following description and claims, when considered in conjunction with the appended drawings.

DETAILED DESCRIPTION OF THE PREFERRED EMBODIMENT

Figure 1:
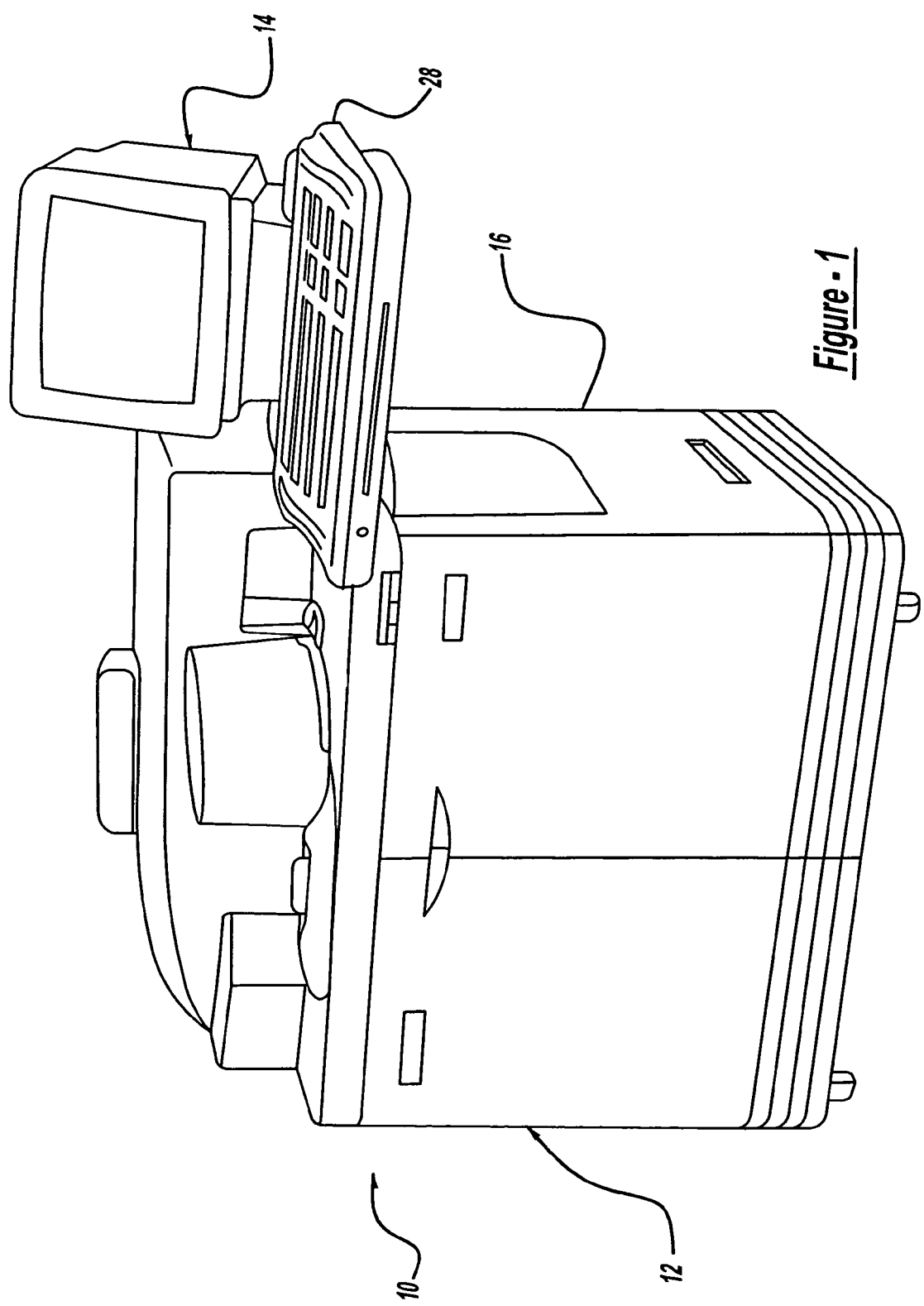
FIG. 1 is an external perspective view of an analyzer system, arranged according to the principles of the present invention.

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, several components of a clinical analyzer are depicted, with one of the preferred embodiments of the present invention being shown generally at 10. The illustrated analyzer 10 is of course only one of many different analyzer designs within the scope of the present invention.

In the illustrated embodiment, the analyzer 10 illustrated in the drawings includes a main operational unit 12 and an operator control unit 14. The operational unit 12 preferably includes an outer housing 16, a sample handling or supply system 18 for holding and organizing a series of primary patient collection containers 20, a sample metering system 22 for aspirating and dispensing portions of individual samples 24 and moving them among the various operating stations of the analyzer 10, and a sample processing system 26 for conducting the desired clinical tests on and analysis of the samples 24. The operator control unit 14 preferably includes a monitor and keyboard 28 for operating the analyzer 10 as well as the computers of the analyzer 10, including for example a master computer, scheduling computer, and subsystems computers.

Figure 15:
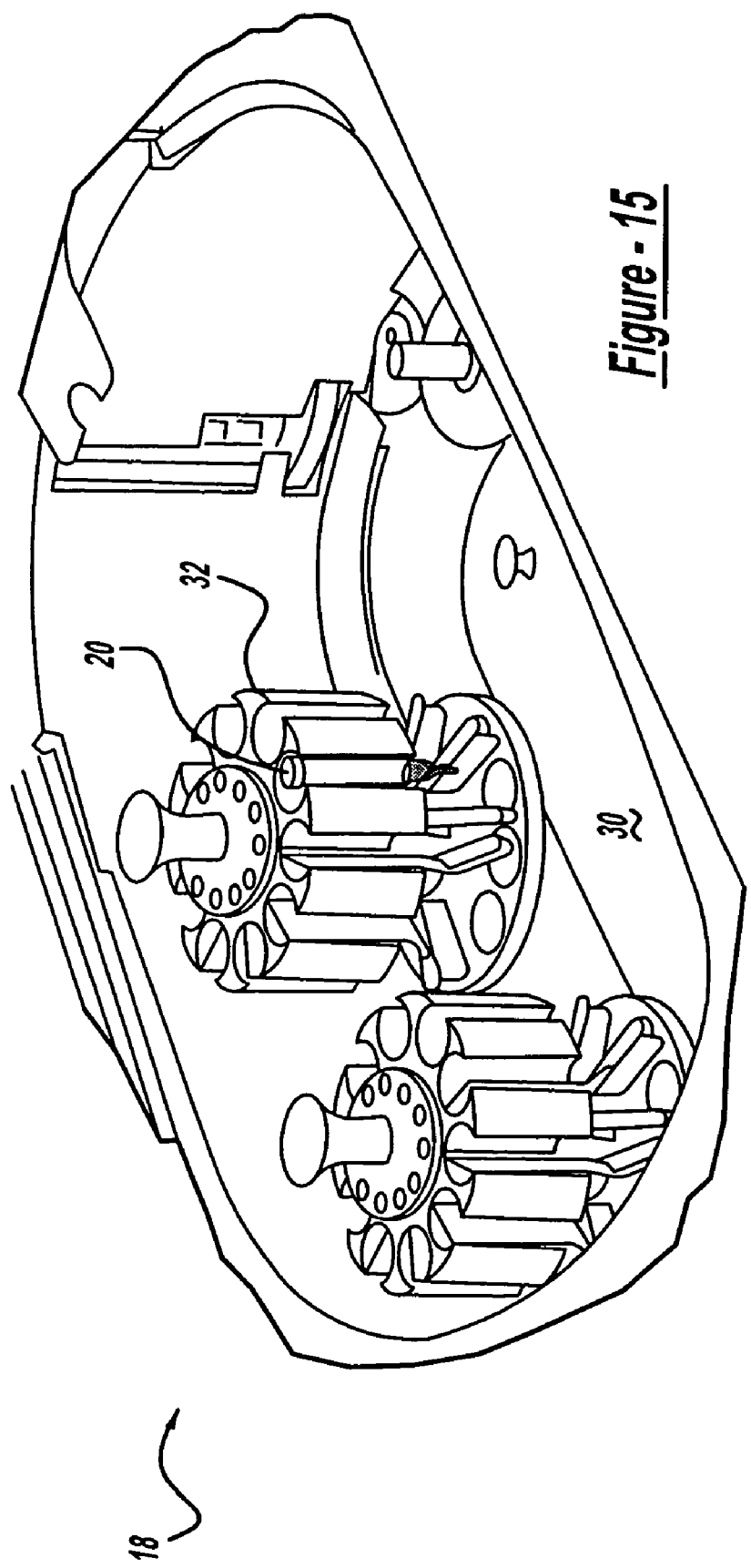
FIG. 15 is a partial perspective view of a clinical chemistry system of an analyzer.

The selection of a particular design for the sample handling system 18 is not important for the present invention, but may include a holding surface or bay 30 for supporting a series of sample trays 32, each holding several primary patient collection containers 20. The sample handling system may be arranged along the lines of the sample handling system 18 shown in FIG. 15, but may of course have a variety of designs. Such other designs may include a rectangular sample bay, linear sample trays, or any other suitable design.

The "primary patient collection container" is a container in which patient biological liquid, usually blood, is initially placed. The container is generally provided a label and processed in preparation for testing. In the case of whole blood, such processing often includes phase separation in which liquid serum or plasma is separated from the cellular phase comprising the blood cells, usually with a gel separation barrier.

Figure 2:
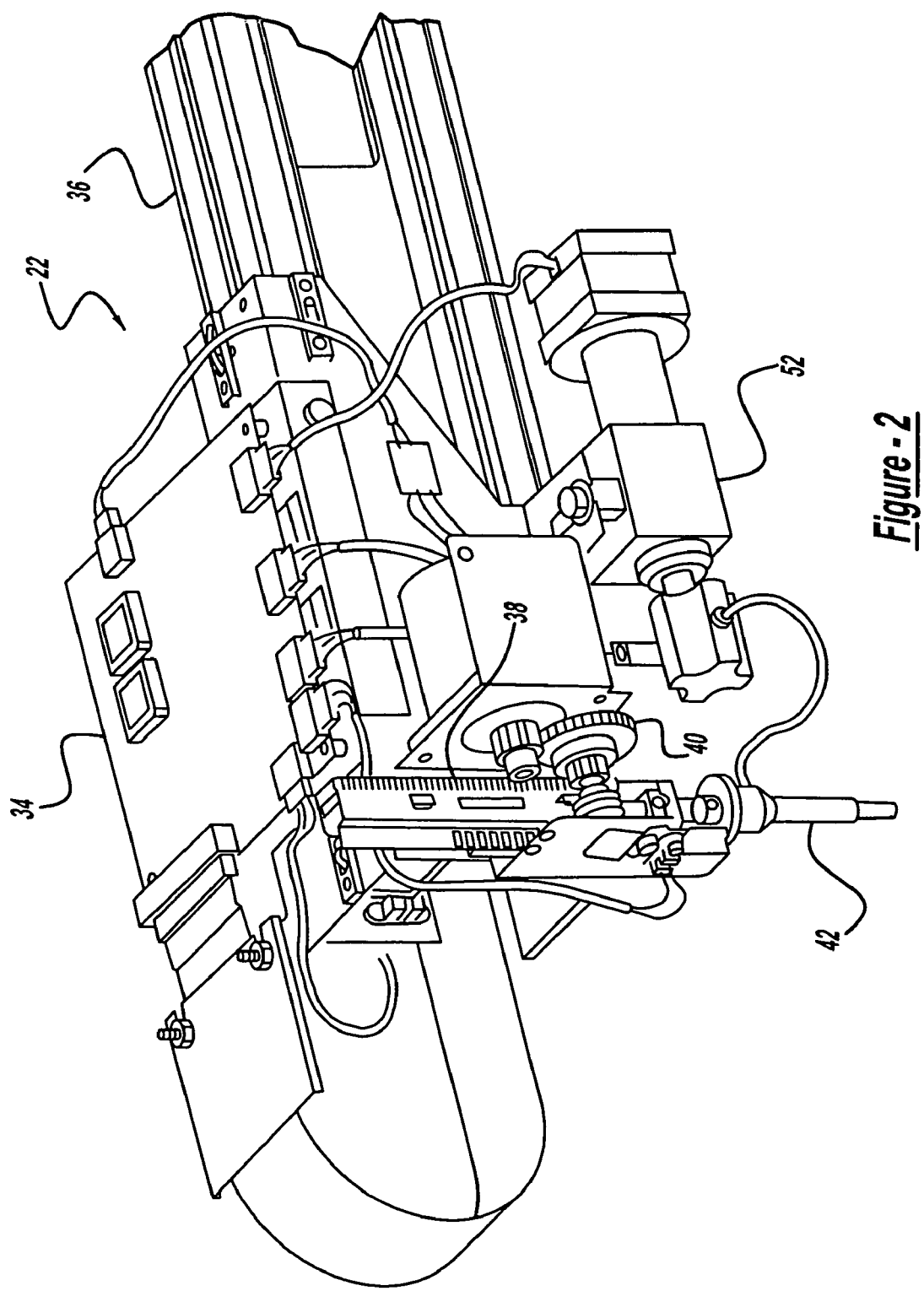
FIG. 2 is a perspective view of a portion of an analyzer system.
Figure 6:
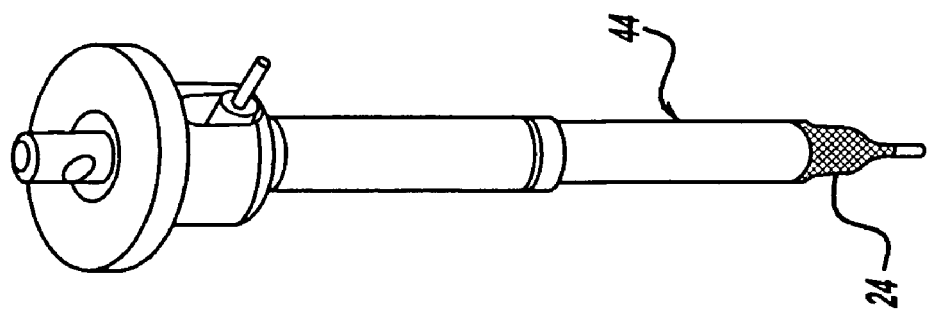
FIGS. 3–9 are partially diagrammatic views of portions of an analyzer system, illustrating operation of the analyzer according to a method of the present invention.

The sample metering system 22 may preferably be arranged along the lines of that shown in FIG. 2, but may also have a variety of designs. The sample metering system 22 shown in FIG. 2 includes a base 34 mounted for selective longitudinal movement on a horizontal rail 36, a horizontal drive mechanism (not shown), a vertical carriage 38 coupled to a vertical drive mechanism 40 for selective vertical movement with respect to the base 34, and a proboscis 42 affixed to the vertical rack 38. Essentially, the proboscis 42 can move in at least two dimensions within a vertical plane defined by the rail 36. Such a metering control system 22 is described in, for example, U.S. Pat. No. 4,340,390.

Because of the sensitive nature of the sample liquid 24, it is desirable to operate the sample metering system 22 without allowing any portion of the proboscis 42 to contact sample liquid 24. Accordingly, the analyzer 10 preferably has a supply of the tubular metering tips 44 which are preferably disposable. The metering tips 44 shown in the drawings can be removably attached to an end of the proboscis 42, and have a tubular body 46, and intermediate cone 48, and a capillary tip 50.

A metering pump 52 is operatively coupled to a lumen defined by the proboscis 42 and the metering tip 44, for selectively generating various amounts of partial vacuum and partial pressure. The metering pump 52, and therefore the metering assembly 22, is capable of using such partial vacuum and partial pressure to selectively aspirate and dispense amounts of sample liquid 24.

As will be readily evident, the material of the metering tips 44 is preferably selected to allow transmission of near-infrared and adjacent visible radiation. The metering tips 44 are preferably free of labels, since any labeling can be done exclusively on the primary collection containers 20. Materials useful for metering tips 44 may include polymers such as polypropylene and polyethylene.

The sample processing system 26 has equipment for performing various clinical chemistry tests, which may include a thin film system having a supply of reagents and test element slides, and/or wet chemistry apparatus, and any other suitable clinical chemistry testing system. The illustrated sample processing system 26 has a supply of thin film slides, rotating incubator 56, reference fluid supply 58, electrometer 60, immuno-wash fluid system 62, and other clinical chemistry equipment shown in the drawings. The sample processing system 26 may include equipment to perform potentiometric, calorimetric or other clinical chemistry tests.

The analyzer 10 preferably includes conventional clinical chemistry for various assays that use test elements. The term "test element" means any reaction vessel in which at least one reagent has been pre-supplied, for example thin film or dry slide test elements. Such slides are described in, for example, U.S. Pat. No. 3,992,158. Another example of a test element would include a cup or well having a cavity pre-coated with one or more antibodies, as is described in U.S. Pat. No. 5,441,895.

In operation, the sample metering system 22 moves about the analyzer 10 among the various operating stations in a cyclical, periodic manner. First, the sample metering system 22 moves from an initial or home position to a position above a tray of disposable metering tips 44, where the proboscis 42 descends into and picks up a metering tip 44 from the tip tray. The sample metering system 22 then moves the proboscis 42 over the sample handling system 18. The proboscis 42 descends and inserts the metering tip 44 into a primary collection container 20. The metering pump 52 creates a partial vacuum, and a portion of the patient sample 24 is aspirated into the tip 44.

Next, the sample metering system 22 moves over a test element, the metering pump 50 creates a partial pressure, and a portion of the sample liquid 24 in the metering tip 44 is dispensed onto the test element. Thereafter, the test element may be transferred to an incubator 56 where it incubates (possibly also with rotation of the incubator), until it is read or detected at a test station. The test station may generally include a colorimetric or potentiometric detector.

Additional steps and processes may be performed by the sample processing system 26 in a conventional manner. When finished, the timing cycle repeats. The time required to complete such a cycle defines the heartbeat of the analyzer.

One proposal that has been considered is to simply incorporate sample quality measurements into the timing cycle of the analyzer, in a serial manner. However, such a serial approach would undesirably lengthen the timing cycle, or require the analyzer to skip a timing cycle to conduct the sample quality measurement. This approach would thus cause an undesirable decrease in analyzer throughput, since the sample quality reading would take as much time as metering a sample onto a new test element.

This approach would also require substantial analyzer software modifications, to enable the proboscis 42 and metering tip 44 to move to a new location where the sample integrity read block is positioned. Also, additional sample fluid would be required, because the level of the sample fluid must be in the cone of the metering tip for an accurate reading.

Accordingly, the sample quality system of the present invention provides the novel concept of conducting the sample quality measurement in a parallel process to the conventional sample processing system. The concept is to have a sample quality device grab the tip as the metering system is about to eject it. This parallel process enables the sample quality system to take several seconds to move the tip into position, make the sample quality reading, and dispose of the tip without impacting the analyzer timing cycle or throughput.

Figure 5:
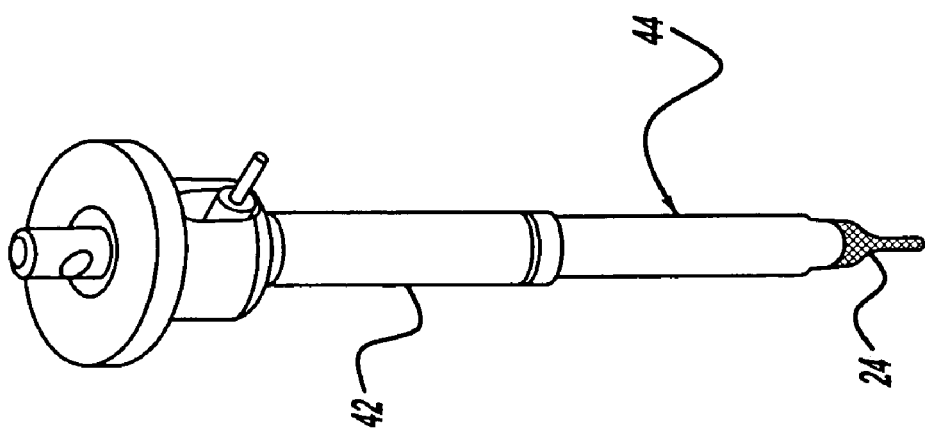
Figure 4:
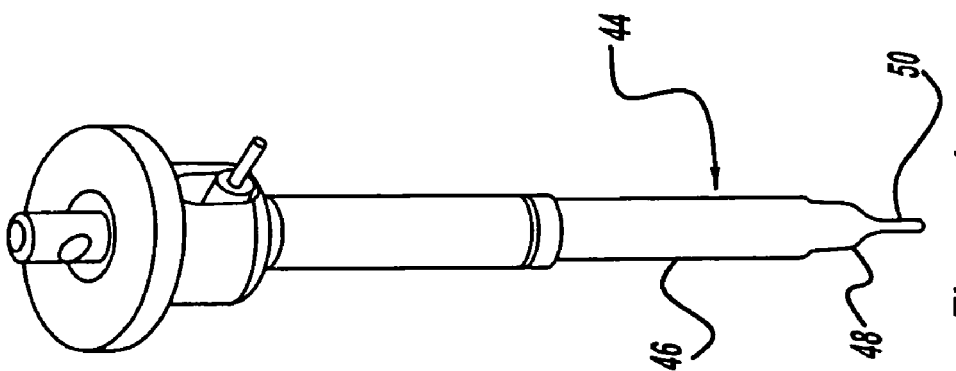
Figure 3:
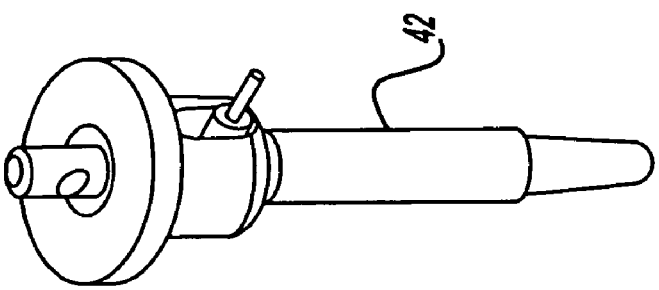

One example of the novel sample quality system 62 of the present invention is shown in the drawings. In particular, operation of a sample quality system 62 is depicted in FIGS. 3–13. FIGS. 3–5 show the proboscis 42 before and after picking up a disposable metering tip 44, and then after some sample liquid 24 has been aspirated into the tip 44.

Another novel feature of the present invention is illustrated in FIGS. 6–9, which occur after the sample processing system 26 has conducted the various operations and tests during a normal timing cycle, and before the tip 44 is removed from the proboscis 42 and eventually discarded. According to this novel feature, the sample quality system 62 will first crimp the end of the tip 44 to prevent sample fluid from being lost during and after the tip ejection process. As a result, the crimped tip essentially becomes a virtual cuvette 64 for holding the sample fluid.

The sample quality system 62 can then perform an absorption measurement while the sample metering system 22 is picking up the next tip 44 and aspirating fluid 24, continuing the primary timing cycle.

Figure 9:
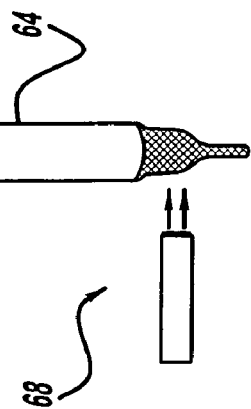
Figure 8:
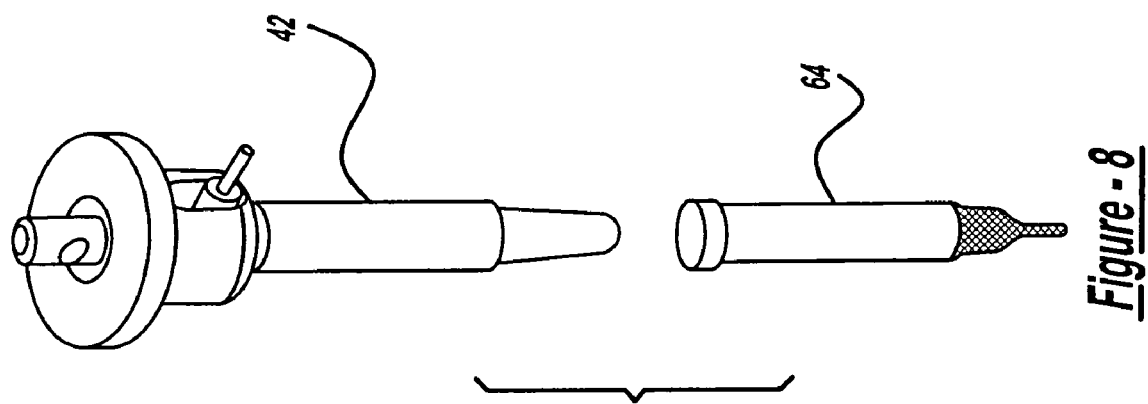
Figure 7:
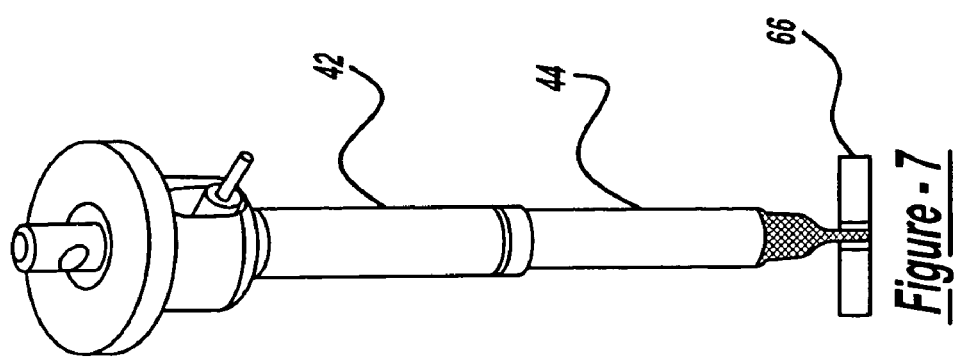
Figure 10:
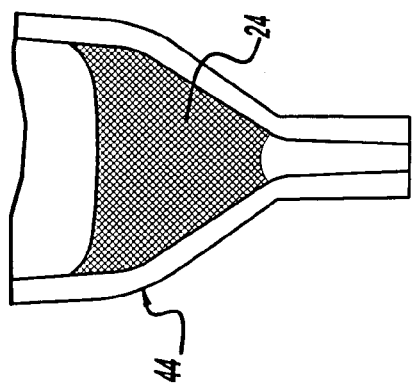
FIGS. 10–13 are partially diagrammatic views of portions of an analyzer system, showing in particular a cone portion of a metering tip during operation of the analyzer according to a method of the present invention.
Figure 11:
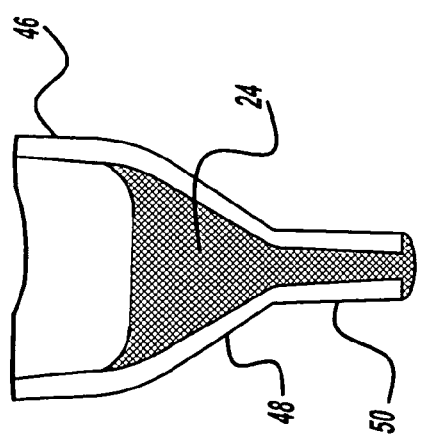
Figure 13:
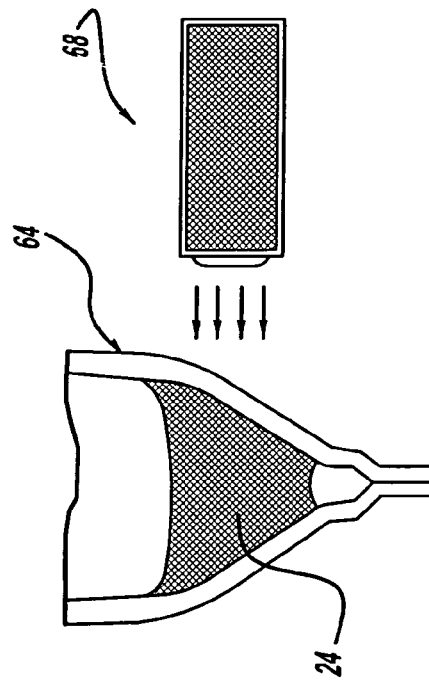
Figure 12:
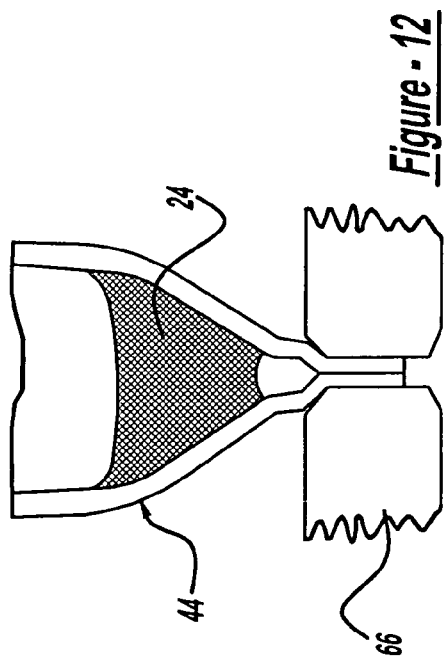
Figure 14:
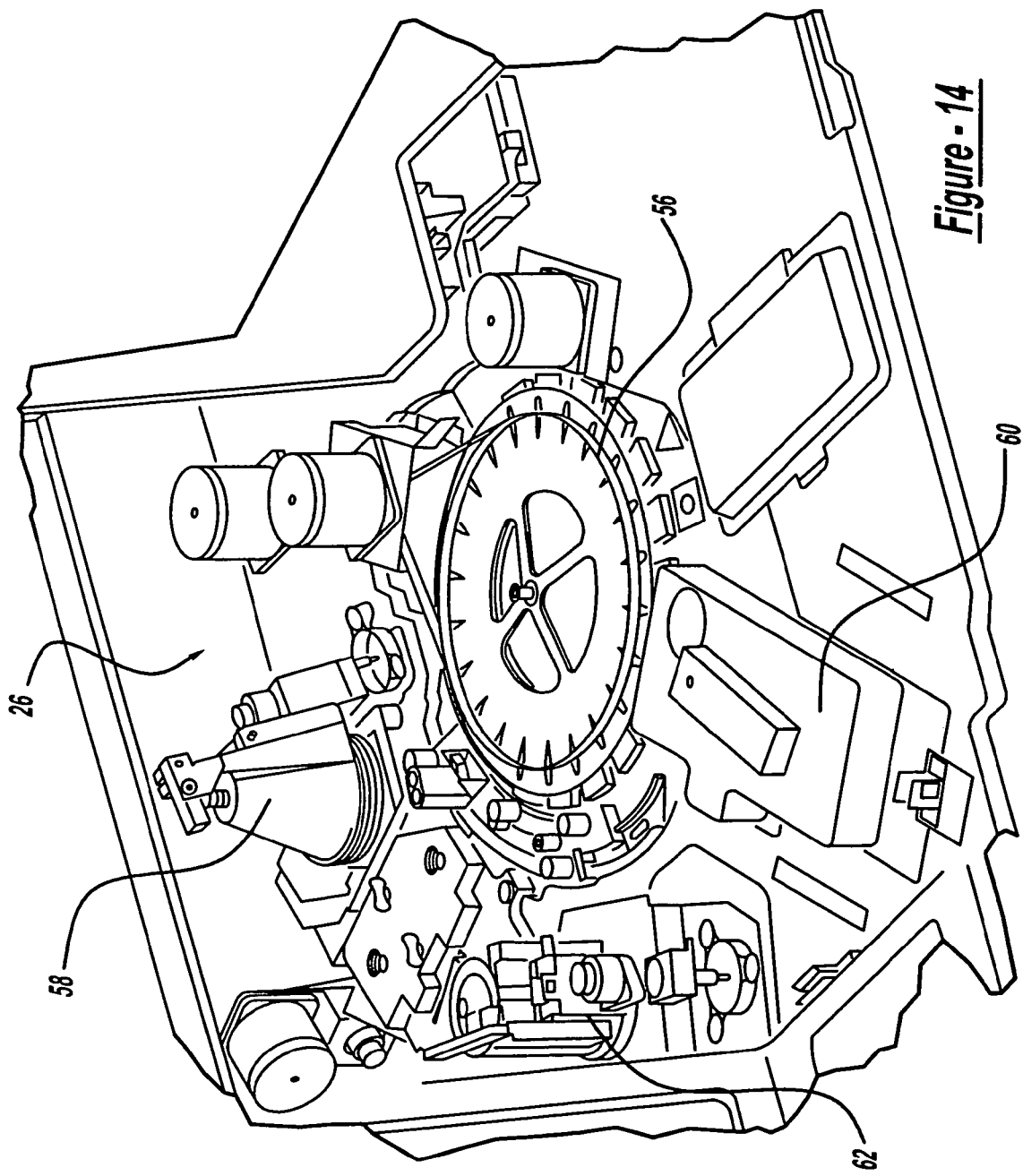
FIG. 14 is a partial perspective view of a sample handling system and a sample metering system of an analyzer.

These additional steps are illustrated in FIGS. 6–9. First, the sample liquid 24 is further aspirated to a slightly higher level in the metering tip 44, leaving a portion of the capillary tip 50 empty of fluid 24. Any suitable type of heated die or clamp 66 may be used to seal a portion of the capillary tip 50. Following removal of the metering tip 44 from the proboscis 42, the metering tip 44 is sealed and becomes a cuvette 64 as shown in FIG. 8, and the sample quality measurement is performed as shown in FIG. 9.

The sample quality measurement of the present invention is performed by a spectrophotometer 68. The spectrophotometer 68 is shown only diagrammatically in the drawings, and it is not described in any detail, because any suitable spectrophotometer may be used, provided it operates acceptably and is preferably responsive to radiation in the near-infrared and adjacent visible light regions with sufficient precision. The term "near-infrared and adjacent visible radiation" or light means radiation between about 400 and 2500 nm, and preferably between about 475 and 1075 nm. Useful translucent or transparent materials for the metering tips that allow desired spectral penetration are those commonly used to manufacture clinical analyzer disposable tips, including polypropylene and polyethylene.

In operation, the cuvette 64 is positioned at the sample quality station, and a beam of preferably near-infrared and adjacent visible wavelengths is passed through the cuvette 64 and any liquid inside. The radiation transmitted is spectrophotometrically analyzed by the spectrophotometer 68. The signal produced by the detector is then correlated with the concentration of target substances.

A preferred set of target substances are those that indicate sample quality, specifically those selected from the group consisting of hemoglobin, lipids, bilirubin, and biliverdin. However, any target substance capable of spectrophotometric detection by its absorption spectra can be correlated and detected by this invention. More specifically, certain assays that have previously been conducted on the slide test element, can now be conducted through the tip spectrophotometrically.

In addition to testing for sample quality, any target substance that is analyzable spectrophotometrically, preferably by using near-infrared and adjacent visible wavelengths, can be analyzed by the spectrophotometer while the patient sample is in the metering tip. Such possible target substances include hemoglobin, albumin and glucose, among others. By testing these target substances in the tip, it is not necessary to conduct (and the analyzer preferably omits), further assays for them when the sample is tested by the sample processing system during the normal timing cycle.

This technique enhances greatly the total throughput of the analyzer 10, because the spectrophotometric detection is performed in a parallel process from the standard analyzer process. Also, the spectrophotometric measurement through the tip 44 may require only about four seconds for all the target substances, compared to about four seconds for each separate assay performed on a slide test element. In addition, the "time to result" is also improved by spectrophotbmetric analysis through the tip to approximately four seconds for analysis through the tip, compared to approximately five minutes on a slide test element.

Testing in this manner while sample liquid is in the metering tip may also be done with some kind of temperature control. Such sample liquid temperature control may be done by controlling the temperature at the test station, but can also be done by heating or cooling the sample liquid in the primary containers, or while the liquid is in the metering tip, etc.

Although the tests conducted by the sample processing system 26 preferably omits those spectrophotometric tests done through the tip 44, it is also possible to repeat such assays during the primary timing cycle, to obtain a check of their accuracy.

In addition, another optional step of the present invention may involve aspirating a selected auxiliary volume of sample liquid from the tip or cuvette after the sample quality measurement, and passing this auxiliary sample to a wet chemistry analyzer system. Moreover, rather than a wet chemistry system, the auxiliary sample may be passed to a diluter system, where it is diluted and passed on to the sample processing apparatus for repeating at least one clinical chemistry test and analysis on the diluted liquid.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

The invention claimed is:

1. A clinical analyzer for analyzing at least a portion of a liquid sample, comprising:

sample handling apparatus having one or more sample containers holding an amount of sample liquid;

sample metering apparatus having a proboscis defining a metering lumen, one or more tips with a tubular shape and a metering aperture at one end, and a metering pump coupled with the proboscis lumen; the tips being removably attachable to the proboscis and allowing fluid communication between the metering pump and the metering aperture through the proboscis lumen;

sample processing apparatus having one or more test elements, an incubator and at least a thin film clinical chemistry system and a wet chemistry clinical testing system for conducting clinical tests on the liquid samples; and sample quality apparatus having a spectrophotometer and a tip end clamping device;

the analyzer having several operating stations:

(a) an initial aspiration position where a metering aperture of the tip can be periodically immersed in sample liquid held within one of the sample container; the metering pump adapted to create a partial vacuum to cause a selected volume of sample liquid to be aspirated from a sample container into the tip;

(b) a dispensing position where the metering pump can create a partial pressure to cause a portion of the sample liquid to be dispensed from the tip onto a test element;

(c) a thin film clinical chemistry testing position;

(d) a sample quality measurement position; and (e) a wet chemistry testing position.

* * * * *